United States Patent [19]

Kadin

[11] 4,017,625
[45] Apr. 12, 1977

[54] ANTI-ALLERGIC N-(5-TETRAZOLYL)-1-OXO-1H-6-ALKOXYPYRIMIDO-[1,2-a]QUINOLINE-2-CARBOXAMIDES AND INTERMEDIATES THEREFOR

[75] Inventor: Saul B. Kadin, New London, Conn.

[73] Assignee: Pfizer Inc., New York, N.Y.

[22] Filed: May 24, 1976

[21] Appl. No.: 689,579

Related U.S. Application Data

[63] Continuation-in-part of Ser. No. 601,039, Aug. 1, 1975, abandoned.

[52] U.S. Cl. .......................... 424/251; 260/256.4 F
[51] Int. Cl.$^2$ ...................................... C07D 401/14
[58] Field of Search .............. 260/256.4 F; 424/251

[56] References Cited

UNITED STATES PATENTS

| | | | |
|---|---|---|---|
| 3,743,733 | 7/1973 | Houlihan | 424/251 |
| 3,792,050 | 2/1974 | Hodson et al. | 424/251 |
| 3,925,384 | 12/1975 | Krapcho et al. | 424/251 |

Primary Examiner—Donald G. Daus
Assistant Examiner—James H. Turnipseed
Attorney, Agent, or Firm—Connolly and Hutz

[57] ABSTRACT

A novel series of N-(5-tetrazolyl)-1-oxo-1H-6-alkoxypyrimido[1,2-a]quinoline-2-carboxamides of the formula

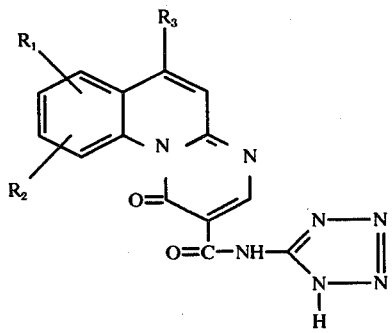

wherein each of $R_1$ and $R_2$ is hydrogen, lower alkyl, lower alkoxy, fluoro or chloro; $R_3$ is chloro, bromo or lower alkoxy; $R_1$ and $R_2$ when taken together are alkylenedioxy of one to two carbon atoms; intermediates therefor and the pharmaceutically-acceptable cationic salts thereof; and their use as anti-allergy agents.

25 Claims, No Drawings

ANTI-ALLERGIC N-(5-TETRAZOLYL)-1-OXO-1H-6-ALKOXYPYRIMIDO-[1,2-a]QUINOLINE-2-CARBOXAMIDES AND INTERMEDIATES THEREFOR

CROSS-REFERENCE TO RELATED APPLICATIONS

This application is a continuation-in-part of copending application Ser. No. 601,039, filed Aug. 1, 1975, now abandoned.

BACKGROUND OF THE INVENTION

1. Field of the Invention

This invention relates to N-(5-tetrazolyl)-pyrimido[1,2-a]quinoline-2-carboxamides and derivatives thereof and to their use as antiallergy agents. More particularly, it relates to N-tetrazolyl-1-oxo-1H-6-($R_3$-substituted)-pyrimido[1,2-a]quinoline-2-carboxamides wherein the 6-substituent is chloro, bromo or lower alkoxy; pharmaceutically-acceptable cationic salts thereof; and derivatives of such compounds wherein the benzenoid ring bears one or more substituents, which are useful as agents for the treatment of allergic reactions, and especially of allergic bronchial asthma; and intermediates therefor.

2. Description of the Prior Art

Allergic reactions, the symptoms resulting from an antigen-antibody interaction, manifest themselves in a wide variety of ways and in different organs and tissues. Common allergic disorders, for example, are allergic rhinitis, a condition characterized by seasonal or perennial sneezing, running nose, nasal congestion, with itching a congestion of eyes; hay fever, a variety of allergic rhinitis that results from hypersensitivity to grass pollens; and bronchial asthma, one of the most disabling and debilitating of allergic reactions, a disease characterized by hyper-reactivity of the bronchi on exposure to various immunogenic or nonimmunogenic stimuli, resulting in bronchospasms with wheezing, short-lived paroxysms and widespread constriction of airway passages. The mechanical obstruction to airflow in airways is generally reversed by the use of bronchodilators, which provide symptomatic relief. In contrast, antiallergy agents prevent the release of mediators of anaphylaxis from tissue stores, thereby acting in a prophylactic manner to preclude elicitation of bronchoconstriction by the mediators.

Efforts to discover medicinal agents to alleviate the symptoms of the abnormal physiologic state have been extensive. As early as 1910, Matthews, *Brit. Med. J.*, 1, 441 (1910) reported the bronchodilator effects of epinephrine. Since then, Chen and Schmidt, *J. Pharmacol. Exper. Therap.*, 24, 339 (1924) reported the use of the alkaloid ephedrine as an orally efficacious bronchodilator with the same spectrum of activity as epinephrine. In 1940, Konzett, *Arch. Exp. Path. Pharmak.*, 197 27 (1940) outlined the effects of the potent aerosol bronchodilator isoproterenol. Cullum et al., *Brit. J. Pharmacol. Exp.*, 35, 141 (1969) reported the pharmacology of salbutamol, a potent bronchodilator of prolonged duration, and active via both oral and aerosol administration. Many bronchodilator preparations contain theophylline. These are generally less potent that the sympathomimetic amines such as isoproterenol and salbutamol, and are ineffective in aerosol administration.

Recently, Cox and co-workers, *Adv. in Drug Res.*, 5, 115 (1970), described the pharmacology of one such agent, disodium cromoglycate [1,3-bis(2-carboxycromon-5-yloxy)-2-hydroxypropane, Intal]. It is not a bronchodilator, but mediates its therapeutic effects by a unique mechanism of action involving inhibition of release of mediators of anaphylaxis and is administered prophylactically. It suffers from lack of oral efficacy and, for optimum results, is administered by inhalation as a solid inhalant. Further, although it is effective against anaphylaxis due to immunoglubulin E (IgE), it is effective against anaphylaxis due to immunoglubulin G (IgG) only at high doses (60–70% protection at 100 and 300 mg./kg.).

Although the aforementioned agents represent outstanding contributions toward the treatment of asthma, many of them exert the undesired side effect of cardiac stimulation.

The synthesis of a 1H-pyrimido[1,2-a]quinoline appears to have first been reported by Antaki et al., *J. Chem. Soc.*, pages 551–555 (1951), who condensed 2-chloroquinoline with ethyl β-amino crotonate in the presence of anhydrous potassium carbonate and a trace of copper bronze to produce 1-oxo-1H-3-methyl-pyrimido[1,2-a]quinoline. No utility for the compound was reported.

Antaki, *J. Am. Chem. Soc.*, 80, 3066-9 (1958) reports the condensation of 2-aminoquinoline and ethylethoxymethylenecyanoacetate to give ethyl 2-quinolylaminomethylenecyanoacetate which when distilled under reduced pressure afforded 1-oxo-1H-pyrimido[1,2-a]quinoline-2-carbonitrile. The compound demonstrated antischistosomal action.

Richardson, et al., *J. Med. Chem.*, 15, 1203-6 (1972) describe ethyl 1-oxo-1H-pyrimido]1,2-a]quinoline-2-carboxylate and report it to be inactive as an antimicrobial agent. When tested for antiallergy activity by the PCA test it was found to exhibit 100% inhibition at 3 mg./kg. by the intravenous (I.V.) route of administration but is without activity at 1 mg./kg. I.V. Approximately 90% inhibition is demonstrated at 30 mg./kg. by the oral route of administration, but oral activity is absent at a dosage level of 10 mg./kg. via the oral route.

SUMMARY OF THE INVENTION

It has now been found that compounds having the formula

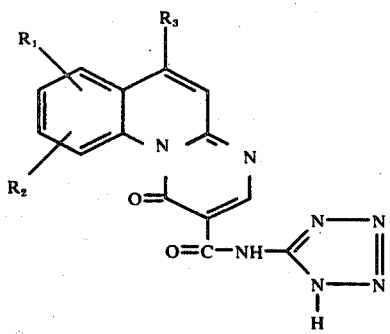

are valuable antiallergy agents; that is, agents which inhibit the release of mediators of anaphylaxis, in mammals, including man, and in this way preclude elicitation of bronchoconstriction by the mediators. They are not bronchodilators. They are, in contrast to disodium cromoglycate, of practical value against both IgG and IgE mediated anaphylaxis via the oral, intranasal and intraperitoneal routes of administration, and by inhalation. In this formula, each of the benzenoid substituents and $R_1$ and $R_2$ is selected from the group consisting of hydrogen, lower alkyl, lower alkoxy, fluoro and chloro;

$R_1$ and $R_2$ when taken together are alkylenedioxy of 1 to 2 carbon atoms and are selected from the group consisting of methylenedioxy and ethylenedioxy;

$R_3$ is selected from the group consisting of chloro, bromo and lower alkoxy;

and the pharmaceutically-acceptable cationic salts thereof.

The terms "lower alkyl" and "lower alkoxy" as used herein are intended to refer to alkyl and alkoxy groups having from one to five carbon atoms since the reactsnts necessary to prepare such compounds are more readily available than are those having larger alkyl or alkoxy groups.

By the term "pharmaceutically-acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as triethylamine, trin-butylamine, piperidine, triethanolamine, diethylaminoethylamine, N,N'-di-benzylethylenediamine and pyrrolidine.

The 5-substituted tetrazoles, as is known, can exist in two isomeric forms, viz:

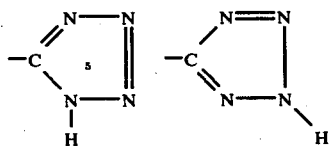

which co-exist in a dynamic tautomeric, equilibrium mixture. Both forms of the tetrazolyl amides are included within the scope of this invention.

The antiallergy activity of the corresponding acids; namely, 1-oxo-1H-6-alkoxypyrimido[1,2-a]quinoline-2-carboxylic acids and esters thereof, is described in U.S. application Ser. No. 554,966, filed Mar. 3, 1975, and now abandoned. The compounds described herein exhibit a significantly broader spectrum of anti-allergy activity than do the corresponding acids and esters. Their anti-allergy activity than do the corresponding acids and esters. Their anti-allergy activity is indeed surprising since the corresponding simple amides [e.g., $-CONH_2$, $-CON(C_2H_5)_2$] are inactive as antiallergy agents when tested by the methods described below.

Compounds of particular interest to this invention are those wherein $R_3$ is methoxy or ethoxy and the benzenoid variables ($R_1$, $R_2$) are hydrogen and those wherein $R_3$ is methoxy and at least one of the benzenoid substituents is lower alkoxy or fluoro, the remaining benzenoid substituent being hydrogen.

| $R_1$ | $R_2$ | $R_3$ |
|---|---|---|
| H | H | $OCH_3$, $OC_2H_5$ |
| H | $CH_3$ | $OCH_3$, $OC_2H_5$ |
| H | $OCH_3$ | $OCH_3$ |
| H | $OC_2H_5$ | $OCH_3$ |
| H | F | $OCH_3$ |

The antiallergy property of the compounds of this invention is evaluated by the passive cutaneous anaphylaxis (PCA) test (Ovary, J. Immun., 81, 355, 1958). In the PCA test, normal animals are injected intradermally (i.d.) with antibodies contained in serum obtained from actively sensitized animals. The animals are then challenged intravenously with antigen mixed with a dye such as Evans' Blue. The increased capillary permeability caused by the antigen-antibody reaction causes the dye to leak from the site of the antibody injection. The test animals are then asphyxiated and the intensity of the reaction determined by measuring the diameter and intensity of the blue coloration on the inner surface of the animals' skin.

DETAILED DESCRIPTION OF THE INVENTION

The compounds of this invention are conveniently prepared by dehydrative coupling of the appropriate 1-oxo-1H-6-($R_3$-substituted)pyrimido[1,2-a]-quinoline-2-carboxylic acid with 5-aminotetrazole. The dehydrative coupling is accomplished by means of a wide variety of agents commonly used in peptide syntheses. Representative agents include N,N'-carbonyldiimidazole, N,N'-carbonyl-di-s-triazine, ethoxyacetylene, 1,1-dichlorodiethylether, diphenylketene p-tolylimine, N-hydroxyphthalimide, N-hydroxysuccinimide, N-hydroxypiperidine, ethylene chlorophosphite, diethyl ethylene pyrophosphite, N-ethyl-5-phenylisoxazolium-3'-sulfonate, phenylphosphorodi-(1-imidazolate) and carbodiimides such as dicyclohexylcarbodiimide, 1-cyclohexyl-3-(2-morpholinomethyl)carbodiimide, N-(3-dimethylaminopropyl)-N'-ethylcarbodiimide hydrochloride, 1-ethyl-3-(3'-dimethylaminopropyl)carbodiimide hydrochloride and diethyl cyanamide.

The above-described coupling agents are generally reacted first with the acid reactant and the resulting product then reacted without isolation with 5-aminotetrazole to afford the desired N-(5-tetrazolyl)-1-oxo-1H-6-($R_3$-substituted)pyrimido[1,2-a]quinoline-2-carboxamides. The reaction is carried out in a reaction-inert solvent system in which the acid reactant need not be soluble. The only requirement for the solvent system is that it not enter into any appreciable reaction with the reactants or products. The variety of coupling agents which can be used to bring about the dehydrative coupling allow a wide choice of solvents. Representative solvents are N,N-dimethylformamide, tetrahydrofuran, dioxane, methylene chloride, nitromethane and acetonitrile.

The reaction of the acid reactant with the coupling agent is conducted at a temperature of from about 20° C. to about 110° C. The reactive intermediate is then reacted with 5-aminotetrazole at from about 20° C. to 110° C. Each of these steps is advantageously carried out at from about 50° C. to about 100° C. since the rate and yield of the reaction are improved.

The molar ratio of acid:coupling agent:5-aminotetrazole is generally about 1:1:1 to about 1:1.1:1.1. Higher ratios of coupling agent and 5-aminotetrazole can be used but offer no advantages. Excesses of ten mole percent are satisfactory.

As those skilled in the art will recognize, all reactants can be added at once rather than in stepwise fashion as described above. However, prior formation of the reactive intermediate (acid-coupling agent product) normally produces better yields of desired N-(5-tetrazolyl)amides.

A favored coupling agent is N,N'-carbonyldiimidazole since it affords a smooth reaction and reasonable yields of desired product without optimization of reaction conditions. When using this coupling agent, N,N-dimethylformamide and a temperature of from 85° C. to 100° C. are preferred conditions for reasons mentioned above.

The compounds wherein $R_3$ is alkoxy are also conveniently prepared by the Williamson reaction between the appropriate N-(5-tetrazolyl)-1-oxo-1H-6-chloro(or bromo)pyrimido[1,2-a]quinoline-2-carboxamide and the appropriate alkanol as exemplified herein.

The required 1-oxo-1H-6-($R_3$-substituted)-pyrimido[1,2-a]quinoline-2-carboxylic acids are prepared by condensation of the appropriate 2-amino-4-($R_3$-substituted)quinoline with the appropriate dialkyl ethoxymethylenemalonate to produce the corresponding intermediate dialkyl 4-($R_3$-substituted)-2-quinolylaminomethylenemalonate which is then cyclized to the desired alkyl 1-oxo-1H-6-($R_3$-substituted)-pyrimido[1,2-a]quinoline-2-carboxylate.

The condensation is carried out by heating a stoichiometric mixture of the 2-aminoquinoline reactant and the dialkyl ethoxymethylenemalonate at a temperature of from about 80° C. to about 125° C. Lower temperatures are not desirable because the reaction proceeds at too slow a rate. Higher temperatures can be used but appear to offer no advantages. The reaction is thus conveniently carried out as a melt. It can, of course, be conducted in a solvent or mixture of solvents; for example, ethanol, N,N-dimethylformamide, acetonitrile. However, from a practical standpoint a solvent appears unnecessary.

The intermediate dialkl 4-($R_3$-substituted)-2-quinolylaminomethylenemalonate thus produced is then cyclized, preferably thermally, by heating to a temperature of from about 175° C. to about 250° C. in a suitable reaction-inert diluent; that is, in a compound which permits control of the reaction temperature, is stable to the relatively high temperatures employed and which does not react with the starting material or the products of cyclization. Representative of such diluents are high boiling hydrocarbons such as perhydronaphthalene, mineral oil, diethylbenzene, acetic anhydride containing sulfuric acid, diphenyl ether and diphenyl, especially that which contains 26.5% diphenyl and 73.5% diphenyl ether and is sold under the trade mark Dowtherm A.

The alkyl 1-oxo-1H-6-($R_3$-substituted)pyrimido[1,2-a]quinoline-2-carboxylates are converted to the corresponding acids by hydrolysis, preferably acid hydrolysis. The usual conditions comprise heating an aqueous mixture of the appropriate ester and a mineral acid such as hydrochloric, sulfuric, phosphoric or nitric acids, from about 50° C. to about 100° C. for periods of up to four hours or until hydrolysis is essentially complete. The favored mineral acid is hydrochloric acid of from 3N to 12N concentration. The less soluble the ester reactant in water, the more concentrated the acid used for hydrolysis. The free acids generally crystallize from the hydrolysis reaction mixture upon cooling and are recovered by filtration. When crystallization does not occur the acids are recovered by evaporation of the reaction mixture. The acids are purified by recrystallization from suitable solvents, such as N,N-dimethylformamide.

Salt formation is accomplished by reacting the appropriate acid with the appropriate metal salt, such as a carbonate, bicarbonate, acetate, hexanoate, hydroxide, in suitable medium such as water, methanol or ethanol according to well-known procedures. The salts are recovered by standard methods such as by filtration if they are insoluble in the medium, by evaporation of the solvent if they are soluble in the medium or by precipitation by addition of a non-solvent for the salt.

As noted above, the N-(5-tetrazolyl)amides of this invention exhibit a significantly broader spectrum of antiallergy activity than do the precursor acids. The acids are effective in inhibiting only anaphylactic phenomena mediated by immunoglobin E (IgE). In contrast, the N-(5-tetrazolyl)amides are not only effective against reaginic induced anaphylaxis (IgE, immunoglobin E), but also against immunoglobin G (IgG) induced anaphylaxis. This behavior is also in contrast to the action of disodium cromoglycate which does not inhibit IgG-mediated responses except at high doses.

The products of this invention and the pharmaceutically-acceptable cationic salts thereof are useful as prophylactic agents to inhibit or prevent the release of mediators of anaphylaxis (allergy, immediate hypersentitivity reactions) and the occurrence of allergic symptoms im mammals, and can be administered for such uses individually or as mixtures with other agents; for example, with theophylline or sympathomimetic amines. They can be administered alone, but are generally administered with a pharmaceutical carrier selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine and chloroform and their combinations can be employed as well as other materials.

For the purpose of parenteral administration and inhalation, solutions or suspensions of these compounds in sesame or peanut oil or aqueous propylene glycol solutions can be employed, as well as sterile aqueous solutions of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

The compounds can be administered to asthmatic subjects suffering from bronchoconstriction by means of inhalators or other devices which permit the active compounds to come into direct contact with the constricted areas of the tissues of the subject. When administered by inhalation, the compositions can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g., lactose) for administration from a powder inhalation device. Compositions suitable for inhalation by means of a conventional nebulizer will comprise about 0.1 to about 1% of active ingredient; and those for use in pressurized containers will comprise from about 0.5 to about 2% of active ingredient. Compositions for use as powder inhalants can comprise ratios of active ingredient to diluent jof from about 1:0.5 to about 1:1.5.

It is necessary that the active ingredient form a proportion of the composition such that a suitable dosage form will be obtained. Obviously, several dosage unit forms can be administered at about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95, or an even higher percentage by weight of the active ingredient.

As regards the dosage regimen of the compounds of this invention, the physician will ultimately determine the dosage which will be most suitable for a particular individual, and it will vary with age, weight and response of the particular patient as well as with the nature and extent of the symptoms, the pharmacodynamic characteristics of the particular agent to be administered and the route of administration chosen. Generally, small doses will be administered initially, with a gradual increase in the dosage until optimum level is determined. It will often be found that when the composition is administered orally, larger quantities of the active ingredient will be required to produce the same level as produced by a small quantity administered parenterally.

Having full regard for the foregoing factors, it is considered that an effective daily oral dosage of the compounds of the present invention in humans of from about 10 to about 1500 mg. per day, with a preferred range of about 10 to about 600 mg. per day in single or divided doses, or at about 0.2 to about 12 mg./kg. of body weight will effectively alleviate bronchoconstriction in human subjects. These values are illustrative and there may, of course, be individual cases where higher or lower dose ranges are merited.

When administered intravenously or by inhalation, the effective daily dose is from about 0.5 to about 400 mg. per day, and preferably from about 0.25 to 200 mg. per day, or at about 0.005 to 4 mg./kg. of body weight in single or divided doses.

The same two basic changes are present in cases of anaphylactic shock: (1) an increase in permeability of capillaries, and (2) concentration of smooth muscle. The increased capillary permeability is the result of antigenantibody interaction. It, and smooth muscle contraction, can be observed and readily measured. This increase in capillary permeability forms the basis of the PCA test.

The PCA test is a measure of the anti-allergic (especially antiasthmatic) activity of a compound. Compounds which inhibit a positive PCA test induced by the rat immunochemical counterpart of human immunoglobulin E (IgE), or reagin, are considered to have anti-allergic activity (C. Mota, *Ann. N.Y. Acad. Sci.*, 103, 264 (1963). (Reagin is primarily immunoglobulin E [IgE] and is the principal immunoglobulin responsible for allergic asthma, anaphylaxis, hay fever, food sensitivities and certain manifestations of drug sensitivities). Such compounds when administered to a sensitized subject, human or animal, prior to the time when the subject comes into contact with antigens or substances to which it is allergic, will prevent the allergic reaction which would otherwise occur. They, therefore, provide a method for the prophylactic treatment of allergy or anaphylactic reactions of a reagin mediated nature.

To put it another way, such compounds block the release of mediators resulting from the antigen-antibody (allergic) reaction as illustrated in the PCA test using rat homocytotropic antibody—a known correlate of human reaginic antibody. Inhibition of reaginic antigen-antibody reactions in rats, the test animal of the PCA test, is regarded as representative of inhibition of human reaginic antigen-antibody reactions which occur during allergic episodes.

The PCA reaction test procedure employed to evaluate the compounds of the present invention demonstrates an excellent correlation between activity for compounds in this test and their utility in the treatment of allergic asthma. The ability of agents to interfere with PCA reactions is measured in male Charles River Wistar rats, 170–210 g. Reaginic antiserum, rich in IgE antibodies is prepared according to Petillo et al., *Int. Arch. Allergy*, 44, 309 (1973). Hyperimmune antiserum rich in IgG antibodies to hen egg albumin is prepared according to Orange, et al., *J. Exptl. Med.*, 127, 767 (1968). Forty-eight hours prior to antigen challenge, the reaginic antiserum is injected intradermally (i.d.) into the shaved skin of a normal rat's back; 5 hours before challenge the hyperimmune antisera is similarly injected. At a third site 60 mcg. histamine dihydrochloride and 0.5 mcg. serotonin creatinine sulfate are injected i.d. just prior to antigen challenge as a check for antihistaminic, antiserotonin and unspecific types of blocckage; the compounds of the instant invention or saline are then administered i.v. and immediately followed by the challenge of 5 mg. egg albumen and 2.5 mg. Evans' Blue dye in saline. In the case of oral administration Evans' Blue dye and egg albumen are given five minutes after administration of the drug. Thirty minutes later the animals are asphysiated using chloroform and the skin of the back removed and reversed for observation. A score is assigned each injection site equal to the product of the diameter of the site in mm. and a grad of 0.1, 0.5, 1, 2, 3 or 4 proportional to intensity of dye coloration. The scores for a given injection site are summed for each group of 5 animals and compared to the saline treated controls. The difference is expressed as percent blockade due to the compound employed.

Compounds representative of those of the present invention are tested for antiallergy activity by the above-described procedure and the resulting activities are reported as the degree (%) of protection. Intal, disodium cromoglycate, a commercial antiallergy agent, is included for comparison.

The compounds tested are of the formula

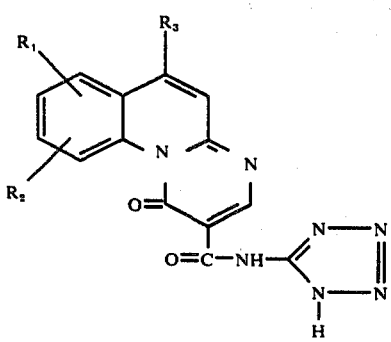

and N,N'-carbonyldiimidazole (357 mg., 2.2 mmole) in N,N-dimethylformamide (15 ml.) is stirred and heated on a steam bath for 15 minutes. A clear solution forms after approximately five minutes' heating, followed by formation of a precipitate. The reaction mixture is stirred an additional 45 minutes at ambient temperature and is then treated with 5-aminotetrazole (187 mg., 2.2 mmole). The mixture is heated on a steam bath for 40 minutes and is then cooled and filtered to recover the product (540 mg. of yellow solid); m.p. 220° C. (dec.).

It is purified by dissolving in hot N,N-dimethylformamide at the rate of 200 mg. crude product per 20 ml. of solvent, filtering the hot solution and then chilling the filtrate. The yellow crystals are filtered and dried; m.p. 255° C. (dec.).

Analysis: Calc'd for $C_{15}H_{11}O_3N_7$: C, 53.41; H, 3.29; N, 29.07%; Found: C, 53.12; H, 3.67; N, 28.75%.

The following compounds are similarly prepared from appropriate reactants:

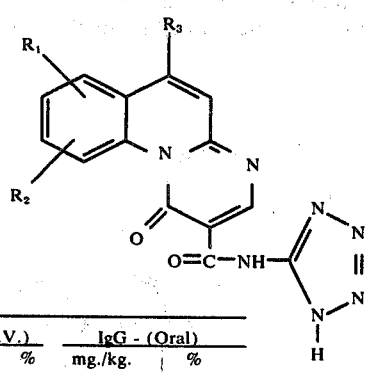

| $R_1$ | $R_2$ | $R_3$ | IgE - (I.V.) mg./kg. | % | IgE - (Oral) mg./kg. | % | IgG - (I.V.) mg./kg. | % | IgG - (Oral) mg./kg. | % |
|---|---|---|---|---|---|---|---|---|---|---|
| H | H | OCH₃ |  |  | 3 | 73 |  |  | 3 | 71 |
|  |  |  |  |  | 0.3 | 17 |  |  | 0.3 | 60 |
| H | H | OC₂H₅ |  |  | 3 | 46 |  |  | 3 | 63 |
|  |  |  |  |  | 1 | 71 |  |  | 1 | 59 |
| H | 8-Cl | OC₂H₅ | 0.3 | 76 | 3 | 28 | 0.3 | 83 | 3 | 19 |
|  |  |  | 0.03 | 8 | 0.3 | 0 | 0.03 | 25 | 0.3 | 0 |
| H | 8-OCH₃ | OCH₃ | 0.3 | 70 | 3 | 54 | 0.3 | 65 | 3 | 51 |
|  |  |  | 0.03 | 74 | 0.3 | 4 | 0.03 | 86 | 0.3 | 4 |
| H | 8-OCH₃ | OC₂H₅ | 0.3 | 100 | 3 | 81 | 0.3 | 69 | 3 | 72 |
|  |  |  | 0.03 | 94 | 0.3 | 17 | 0.03 | 63 | 0.3 | 29 |
| H | 9-OCH₃ | OCH₃ | 0.3 | 97 | 3 | 20 | 0.3 | 85 | 3 | 59 |
|  |  |  | 0.03 | 72 | 0.3 | 1 | 0.03 | 67 | 0.3 | 6 |
| H | 9-F | OCH₃ | 3 | 100 |  |  | 3 | 83 |  |  |
|  |  |  | 0.3 | 100 |  |  | 0.3 | 57 |  |  |
|  |  |  | 0.03 | 89 |  |  | 0.03 | 45 |  |  |
| H | 9-CH₃ | OCH₃ | 0.3 | 70 | 3 | 70 | 0.3 | 55 | 3 | 79 |
|  |  |  | 0.03 | 53 | 0.3 | 7 | 0.03 | 40 | 0.3 | 11 |
| H | 8-C₂H₅ | OCH₃ | 0.3 | 83 | 3 | 81 | 0.3 | 53 | 3 | 75 |
|  |  |  | 0.03 | 8 | 0.3 | 22 | 0.03 | 4 | 0.3 | 12 |

EXAMPLE I

N-(5-Tetrazolyl)-1-oxo-1H-6-methoxypyrimido[1,2-a]-quinoline-2-carboxamide

A mixture of 1-oxo-1H-6-methoxypyrimido[1,2-a]quinoline-2-carboxylic acid (540 mg., 2.0 mmole)

| Example | $R_1$ | $R_2$ | $R_3$ | M.P.(° C.) | Calc'd C | H | N | Found C | H | N |
|---|---|---|---|---|---|---|---|---|---|---|
| II | H | H | OC₂H₅ | 266-8 (d) | 54.70 | 3.73 | 27.91 | 54.59 | 4.11 | 26.50[a] |
| III | H | 8-OCH₃ | OCH₃ | 255-8 (d) | 52.32 | 3.57 | 26.69 | 52.27 | 3.69 | 25.93 |
| IV | H | 8-OCH₃ | OC₂H₅ | 266-8 (d) | 53.54 | 3.96 | 25.71 | 53.63 | 4.01 | 25.55 |
| V | H | 9-CH₃ | OCH₃ | 235-7 (d) | 54.70 | 3.73 | 27.91 | 54.15 | 4.15 | 27.05[b] |
| VI | H | 8-C₂H₅ | OCH₃ | 254-6 (d) | 55.88 | 4.14 | 26.84 | 55.14 | 4.21 | 26.42 |
| VII | H | 8-Cl | OC₂H₅ | 273-6 (d) | 49.82 | 3.13 | 25.42 | 49.53 | 3.38 | 25.41 |
| VIII | H | 9-F | OCH₃ | 235-6 (d) | 50.70 | 2.84 | 27.60 | 50.32 | 3.21 | 26.98[b] |

-continued

| Example | $R_1$ | $R_2$ | $R_3$ | M.P.(° C.) | Calc'd C | Calc'd H | Calc'd N | Found C | Found H | Found N |
|---|---|---|---|---|---|---|---|---|---|---|
| IX | H | 9-OCH$_3$ | OCH$_3$ | 253-4 (d) | 52.32 | 3.57 | 26.69 | 51.64 | 3.62 | 27.43[b] |

[a]average of 3 analyses.
[b]average of 2 analyses.

The product of Example VIII is purified by dissolution in ammonium hydroxide (6N) from which the product precipitates on standing. The solid is filtered, dissolved in water and precipitated from solution by acidification with 3N hydrochloric acid. It is filtered, dried and recrystallized from N,N-dimethylformamide.

The product of Example IX is purified by recrystallization from N,N-dimethylformamide, followed by the purification method accorded the product of Example VIII.

EXAMPLE X

The compounds tabulated are prepared from appropriate reactants by the procedure of Example I.

residue partitioned between 3N hydrochloric acid (25 ml.)—ethyl acetate (100 ml.). The phases are separated and the ethyl acetate phase extracted with 3N hydrochloric acid (2 × 20 ml.). The acid extracts are combined, made neutral (pH 7–8) with 20% ammonium hydroxide and the resulting precipitate recovered by filtration (235 mg.).

The above procedure is repeated but using the β-chloro (or bromo) products of Example X and the appropriate alkanol to give the compounds tabulated below:

| $R_1$ | $R_2$ | $R_3$ |
|---|---|---|
| H | 8-OCH$_3$ | OCH$_3$ |
| H | 8-OCH$_3$ | O-n-C$_4$H$_9$ |
| 8-CH$_3$ | 10-CH$_3$ | OCH$_3$ |
| 7-CH$_3$ | 10-OCH$_3$ | OC$_2$H$_5$ |

| $R_1$ | $R_2$ | $R_3$ | $R_1$ | $R_2$ | $R_3$ |
|---|---|---|---|---|---|
| H | 8-Cl | OCH$_3$ | H | 8-CH$_3$ | OCH$_3$ |
| H | 9-Cl | OCH$_3$ | 8-OCH$_3$ | 9-OCH$_3$ | OCH$_3$ |
| H | 8-OC$_2$H$_5$ | OCH$_3$ | H | 8-F | OCH$_3$ |
| H | 8-OCH$_3$ | Cl | 8-CH$_3$ | 10-CH$_3$ | OCH$_3$ |
| H | 10-OCH$_3$ | Cl | H | 8-i-C$_3$H$_7$ | OCH$_3$ |
| 8-CH$_3$ | 10-CH$_3$ | Cl | 8,9-O—CH$_2$—O— | | OCH$_3$ |
| 7-CH$_3$ | 10-OCH$_3$ | Cl | 9,10-O—CH$_2$—O— | | OCH$_3$ |
| H | 10-Cl | Cl | 7-OC$_2$H$_5$ | 10-OC$_2$H$_5$ | O-n-C$_3$H$_7$ |
| H | 8-Cl | Cl | 8-i-C$_3$H$_7$ | 9-i-C$_3$H$_7$ | OC$_2$H$_5$ |
| H | 9-Cl | Cl | 8,9-O—CH$_2$—O— | | O-n-C$_4$H$_9$ |
| H | 9-CH$_3$ | Br | 8-O-n-C$_3$H$_7$ | 9-Br | OCH$_3$ |
| 8-OCH$_3$ | 9-OCH$_3$ | Br | 8-O-n-C$_4$H$_9$ | 9-O-n-C$_4$H$_9$ | OC$_2$H$_5$ |
| H | H | Br | 7-F | 9-F | OCH$_3$ |
| 8-CH$_3$ | 9-CH$_3$ | Br | 8,9-O—CH$_2$CH$_2$—O— | | OCH$_3$ |
| H | 8-Cl | O-sec-C$_4$H$_9$ | 8,9-O—CH$_2$CH$_2$—O— | | OC$_2$H$_5$ |
| 8-Cl | 9-Cl | OCH$_3$ | 7-t-C$_4$H$_9$ | 10-t-C$_4$H$_9$ | OCH$_3$ |
| H | 9-Cl | O-n-C$_4$H$_9$ | H | 8-OCH$_3$ | OC$_2$H$_5$ |
| H | 8-OCH$_3$ | O-n-C$_4$H$_9$ | H | 8-C$_2$H$_5$ | OCH$_3$ |
| H | 9-OCH$_3$ | O-n-C$_4$H$_9$ | H | 8-Cl | OC$_2$H$_5$ |
| H | H | O-n-C$_3$H$_7$ | | | |
| 7-CH$_3$ | 10-OCH$_3$ | OCH$_3$ | | | |

EXAMPLE XI

N-(5-Tetrazolyl)-1-oxo-1H-6-ethoxypyrimido[1,2-a]-quinoline-2-carboxamide

A mixture of p-toluenesulfonic acid monohydrate (20 mg.) and N-(5-tetrazolyl)-1-oxo-1H-6-chloropyrimido[1,2-a]quinoline-2-carboxamide (1.79 g.) in ethanol (75 ml.) is heated at reflux for 24 hours. The solvent is removed under reduced pressure and the

| | | |
|---|---|---|
| H | 10-Cl | OCH$_3$ |
| H | 8-Cl | OCH$_3$ |
| H | 9-Cl | O-n-C$_3$H$_7$ |
| 8-OCH$_3$ | 9-OCH$_3$ | OC$_2$H$_5$ |
| H | H | OCH$_3$ |

EXAMPLE XII

Salt Formation

The products of Examples I–XI are converted to the sodium, potassium, ammonium, calcium, magnesium, aluminum, triethylamine, tri-n-butylamine, piperidine, triethanolamine, diethylaminoethylamine, pyrrolidine and N,N-dibenzylethylenediamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE XIII

Injectable Preparation

One hundred grams of N-(5-tetrazolyl)-1-oxo-1H-6-methoxypyrimido-[1,2-a]quinoline-2-carboxamide are intimately mixed and ground with 250 grams of sodium ascorbate. The ground, dry mixture is placed in vials and sterilized with ethylene oxide after which the vials are sterilely stoppered. for intravenous administration, sufficient water is added to the materials in the vials to form a solution containing 5.0 mg. of active ingredient per milliliter of injectable solution.

EXAMPLE XIV

Tablets

A tablet base is prepared by blending the following ingredients in the proportion by weight indicated:

| | |
|---|---|
| Sucrose, U.S.P. | 80.3 |
| Tapioca Starch | 13.2 |
| Magnesium Stearate | 6.5 |

Into this tablet base there is blended sufficient N-(5-tetrazolyl)-1-oxo-1H-6-methoxypyrimido[1,2-a]quinoline-2-carboxamide to provide tablets containing 20, 100 and 250 mg. of active ingredient per tablet. The compositions are each compressed into tablets, each weighing 360 mg., by conventional means.

EXAMPLE XV

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient N-(5-tetrazolyl-1-oxo-1H-6,9-dimethoxypyrimido[1,2-a]quinoline:2-carboxamide to provide capsules containing 10, 25 and 50 mg. hard gelatin capsules in the amount of 350 mg. per capsule.

In like manner, capsules containing 2.0 mg. and 6.0 mg. of active ingredient, and having 300 mg. of the following blends per capsule are prepared:

| Ingredients | Weight mg./capsule |
|---|---|
| Drug | 2.00 |
| N-Methylglucamine | 18.00 |
| Lactose, anhydrous | 241.20 |
| Corn starch, anhydrous | 30.00 |
| *Talc | 8.80 |

| Ingredients | Weight mg./capsule |
|---|---|
| Drug | 6.00 |
| N-Methylglucamine | 18.00 |
| Lactose, anhydrous | 237.20 |
| Corn starch, anhydrous | 30.00 |
| *Talc | 8.80 |

*Talc added before encapsulation

EXAMPLE XVI

Solution

A solution of N-(5-tetrazolyl)-1-oxo-1H-6-methoxy-9-fluoropyrimido-[1,2-a]quinoline-2-carboxamide is prepared with the following composition:

| | | |
|---|---|---|
| Effective ingredient | 6.04 | grams |
| Magnesium chloride hexahydrate | 12.36 | grams |
| Monoethanolamine | 8.85 | ml. |
| Propylene glycol | 376.00 | grams |
| Water, distilled | 94.00 | ml. |

The resultant solution has a concentration of effective ingredient of 10 mg./ml. and is suitable for parenteral and, especially for intramuscular administration.

EXAMPLE XVII

An aqueous solution of N-(5-tetrazolyl)-1-oxo-1H-6-methoxypyrimido-[1,2-a]quinoline-2-carboxamide sodium salt (containing 3 mg. of drug per ml. of solution) is placed in a standard nebulizer such as is available from the Vaponephrine Co., Edison, N.J. The solution is sprayed under an air pressure of 6 lbs. per square inch into a closed 8 inch × 8 inch × 12 inch plastic container for six minutes. The container has four openings to accomodate the heads of four rats. Four rats are exposed to the drug simultaneously with only their heads coming in contact with aerosol. The results are evaluated as per the PCA reaction test procedure described above.

EXAMPLE XVIII

Aerosol Suspension

A mixture of N-(5-tetrazolyl)-1-oxo-1H-6-methoxypyrimido[1,2-a]-quinoline-2-carboxamide (antiallergy agent) and the other ingredients under (a) in the examples below are micronized to a particle size of 1 to 5 microns in a ball mill. The resulting slurry is then placed in a container equipped with a valve and propellant (b) introduced by pressure filling through the valve nozzle to a gauge pressure of approximately 35–40 pounds per square inch at 20° C.

| Suspension A | Percent |
|---|---|
| (a) Antiallergy agent | 0.25 |
| Isopropyl myristate | 0.10 |
| Ethanol | 26.40 |
| (b) 60–40% mixture of 1,2-dichlorotetrafluoroethane-1-chloropentafluoroethane | 73.25 |

| Suspension B | Percent |
|---|---|
| (a) Antiallergy agent | 0.25 |
| Ethanol | 26.50 |

| Suspension A | Percent |
|---|---|
| (b) 60–40% mixture of 1,2-dichlorotetrafluoro-ethane-1-chloropentafluoroethane | 73.25 |

PREPARATION A

Ethyl 1-Oxo-1H-6-methoxypyrimido[1,2-a]quinoline-2-carboxylate

1. A mixture of 2-amino-4-methoxyquinoline (34 g., 0.196 mole) and diethyl ethoxymethylenemalonate (46.8 g., 0.216 mole) is heated on a steam bath. A clear melt forms within about 10 minutes and within about 20 minutes begins to resolidify. The mixture is heated a total of 45 minutes and is then cooled. The product, diethyl 4-methoxy-2-quinolylaminomethylenemalonate, is crystallized from ethanol (350 ml.) as a fluffy solid; m.p. 136.5°–137.5° C.

Analysis: Calc'd for $C_{18}H_{20}N_2O_5$: C, 62.78; H, 5.85; N, 8.14%; Found: C, 62.72; H, 6.10; N, 8.37%.

2. To Dowtherm A (350 ml.) at 100° C. is added the product from (1) (55 g., 0.16 mole) and the resulting clear yellow solution heated to 230°–233° C. for 1.75 hours. The reaction mixture is cooled, diluted with ethyl acetate (500 ml.) and then extracted with 1N hydrochloric acid (3 × 120 ml.). The extracts are combined made basic with 20% ammonium hydroxide and chilled to precipitate the product. It is filtered and recrystallized successively from ethanol, benzene-cyclohexane (1:1) and ethanol to give 15.5 g. of yellow crystals; m.p. 130°–130.5° C.

3. Alternatively, the procedure of Preparation A(2) is repeated but starting with 3.5 g. of diethyl 4-methoxy-2-quinolylaminomethylenemalonate. The product is recovered by cooling the reaction mixture, diluting it with cyclohexane (150 ml.) to precipitate the crude product as a brown gummy material. It is obtained in crystalline form by heating the diluted reaction mixture to boiling and filtering the hot mixture. Upon cooling the product precipitates as yellow crystals and is separated by filtration. Yield = 1.1 g. Further purification is achieve by recrystallizing it from ethanol.

PREPARATION B

Following the procedures of Preparation A(1) and A(3), the compounds listed below are prepared from appropriate reactants. In most instances, the product separates in the form of crystals upon dilution of the reaction mixture with cyclohexane and hot filtration of the mixture is unnecessary.

The following are thus prepared:

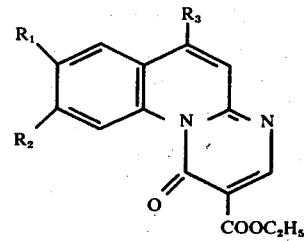

| $R_3$ | $R_1$ | $R_2$ | m.p. (° C.) |
|---|---|---|---|
| $OCH_3$ | Cl | H | 213–214 |
| $OCH_3$ | $CH_3$ | H | 191.5–192.5 |
| $OCH_3$ | $OCH_3$ | H | 200–201.5 |
| $OCH_3$ | H | $OCH_3$ | 184–185 |
| $OCH_3$ | H | Cl | 178–179 |
| $OCH_3$ | H | $CH_3$ | 139–141 |
| $OCH_3$ | $OCH_3$ | $OCH_3$ | 215–216 |
| $OCH_3$ | $OC_2H_5$ | H | 163.5–164.5 |
| $OC_2H_5$ | H | H | 143–145 |
| $OCH_3$ | H | F | 141–143 |
| $OCH_3$ | F | H | 175.5–177 |

PREPARATION C

1-Oxo-1H-6-methoxypyrimido[1,2-a]quinoline-2-carboxylic Acid

A mixture of ethyl 1-oxo-1H-6-methoxypyrimido[1,2-a]quinoline-2-carboxylate (3.0 g.) and concentrated hydrochloric acid (60 ml.) is heated on a steam bath for a half hour. It is then cooled and filtered to give 0.87 g. of the title product. It is recrystallized from N,N-dimethylformamide; m.p. 219° C. (dec.).

In like manner, the products of Preparation B are hydrolyzed to the corresponding acids.

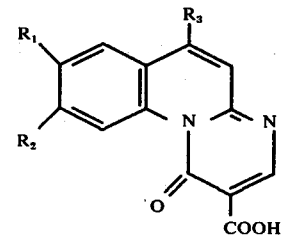

| $R_3$ | $R_1$ | $R_2$ | m.p. (° C.) | |
|---|---|---|---|---|
| $OCH_3$ | Cl | H | 239 | (dec.) |
| $OCH_3$ | $CH_3$ | H | 247 | (dec.) |
| $OCH_3$ | $OCH_3$ | H | | |
| $OCH_3$ | H | $OCH_3$ | 230 | (dec.) |
| $OCH_3$ | H | Cl | 234 | (dec.) |
| $OCH_3$ | H | $CH_3$ | | |
| $OCH_3$ | $OCH_3$ | $OCH_3$ | 245 | (dec.) |
| $OCH_3$ | $OC_2H_5$ | H | 237 | (dec.) |
| $OC_2H_5$ | H | H | 205 | (dec.) |
| $OCH_3$ | H | F | 196–198 | (dec.) |
| $OCH_3$ | F | H | 265–268 | (dec.) |

PREPARATION D

Ethyl 1-Oxo-1H-6-chloropyrimido[1,2-a]quinoline-2-carboxylate

1. A mixture of 2-amino-4-chloroquinoline (15.5 g., 0.087 mole) and diethyl ethoxymethylenemalonate (20.8 g., 0.096 mole) is heated on a steam bath for 45 minutes. Isopropanol (75 ml.) is added to the hot clear melt which is then cooled. The product separates and is filtered, washed with isopropanol and dried. Yield = 26.0 g. of white solid; m.p. 108.5°–109.5° C. It is used directly in step (2) without further purification.

Recrystallization from ethanol affords an analytical sample, m.p. 109°–110° C.

2. The intermediate diethyl 4-chloro-2-quinolylaminomethylenemalonate from step (1) (26 g.) is added to Dowtherm A (75 ml.) at 100° C. The reslting clear solution is heated to 235°–237° C. for 80 minutes and then cooled. Hexane (100 ml.) is added to the reaction mixture and the product which precipitates recovered by filtration, washed with hexane and dried. It is recrystallized from acetonitrile, m.p. 178°–179° C.

The following compounds are prepared from appropriate reactants by the procedures of Preparation D ($R_3$ = Cl, Br) and A(1) and A(3) ($R_3$ = alkoxy) and C:

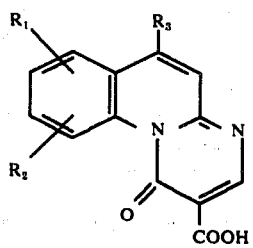

$R_1$ and $R_2$ when taken together are alkylenedioxy and are selected from the group consisting of methylenedioxy and ethylenedioxy;

$R_3$ is selected from the group consisting of chloro, bromo and lower alkoxy;

and the pharmaceutically-acceptable cationic salts thereof.

2. A compound according to claim 1 wherein each of $R_1$ and $R_2$ is hydrogen and $R_3$ is lower alkoxy.

3. A compound according to claim 1 wherein $R_1$ is hydrogen, $R_2$ is 8-lower alkoxy and $R_3$ is ethoxy.

4. A compound according to claim 1 wherein $R_1$ is 8-lower alkoxy, $R_2$ is 9-lower alkoxy, and $R_3$ is methoxy.

5. A compound according to claim 1 wherein $R_1$ is hydrogen, $R_2$ is fluoro and $R_3$ is methoxy.

6. The compound according to claim 2 wherein $R_3$ is methoxy.

7. The compound according to claim 2 wherein $R_3$ is ethoxy.

8. The compound according to claim 3 wherein $R_2$ is 8-methoxy.

9. The compound according to claim 4 wherein $R_1$ is 8-methoxy and $R_2$ is 9-methoxy.

10. The compound according to claim 5 wherein $R_2$ is 9-fluoro.

11. The method of inhibiting the release of mediators of anaphylaxis in a mammalian subject which comprises administering to the subject an anaphylaxis mediator release inhibiting amount of a compound having the formula

| | | | | | |
|---|---|---|---|---|---|
| H | 8-OCH$_3$ | Cl | 8-CH$_3$ | 10-CH$_3$ | OCH$_3$ |
| H | 10-OCH$_3$ | Cl | H | 8-i-C$_3$H$_7$ | OCH$_3$ |
| 8-CH$_3$ | 10-CH$_3$ | Cl | 8,9-O—CH$_2$—O— | | OCH$_3$ |
| 7-CH$_3$ | 10-OCH$_3$ | Cl | 9,10-O—CH$_2$—O— | | OCH$_3$ |
| H | 10-Cl | Cl | 7-OC$_2$H$_5$ | 10-OC$_2$H$_5$ | O-n-C$_3$H$_7$ |
| H | 8-Cl | Cl | 8-i-C$_3$H$_7$ | 9-i-C$_3$H$_7$ | OC$_2$H$_5$ |
| H | 9-Cl | Cl | 8,9-O—CH$_2$—O— | | O-n-C$_4$H$_9$ |
| H | 9-CH$_3$ | Br | 8-O-n-C$_3$H$_7$ | 9-Br | OCH$_3$ |
| 8-OCH$_3$ | 9-OCH$_3$ | Br | 8-O-n-C$_4$H$_9$ | 9-O-n-C$_4$H$_9$ | OC$_2$H$_5$ |
| H | H | Br | 7-F | 9-F | OCH$_3$ |
| 8-CH$_3$ | 9-CH$_3$ | Br | 8,9-O—CH$_2$CH$_2$—O— | | OCH$_3$ |
| H | 8-Cl | O-sec-C$_4$H$_9$ | 8,9-O—CH$_2$CH$_2$—O— | | OC$_2$H$_5$ |
| 8-Cl | 9-Cl | OCH$_3$ | 7-t-C$_4$H$_9$ | 10-t-C$_4$H$_9$ | OCH$_3$ |
| H | 9-Cl | O-n-C$_4$H$_9$ | H | 8-OCH$_3$ | OC$_2$H$_5$ |
| H | 8-OCH$_3$ | O-n-C$_4$H$_9$ | H | 8-C$_2$H$_5$ | OCH$_3$ |
| H | 9-OCH$_3$ | O-n-C$_4$H$_9$ | H | 8-Cl | OC$_2$H$_5$ |
| H | H | O-n-C$_3$H$_7$ | | | |
| 7-CH$_3$ | 10-OCH$_3$ | OCH$_3$ | | | |

What is claimed is:

1. A compound of the formula

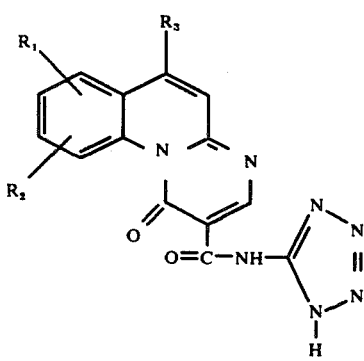

wherein each of $R_1$ and $R_2$ is hydrogen, from the group consisting of hydrogen, lower alkyl, lower alkoxy, chloro, and fluoro;

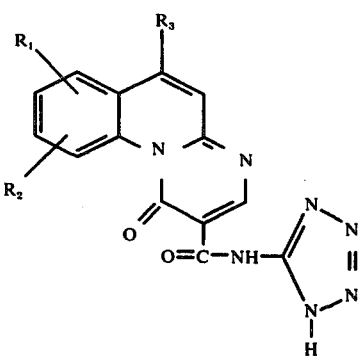

wherein each of $R_1$ and $R_2$ is selected from the group consisting of hydrogen, lower alkyl, lower alkoxy, chloro, and fluoro;

$R_1$ and $R_2$ when taken together are alkylenedioxy and are selected from the group consisting of methylenedioxy and ethylenedioxy;

$R_3$ is selected from the group consisting of chloro, bromo and lower alkoxy;

and the pharmaceutically-acceptable cationic salts thereof.

12. The method according to claim 11 wherein each of $R_1$ and $R_2$ is hydrogen and $R_3$ is lower alkoxy.

13. The method according to claim 11 and wherein $R_1$ is hydrogen, $R_2$ is 8-lower alkoxy and $R_3$ is ethoxy.

14. The method according to claim 11 wherein $R_1$ is hyrogen, $R_2$ is fluoro and $R_3$ is methoxy.

15. The method according to claim 12 wherein $R_3$ is methoxy.

16. The method according to claim 13 wherein $R_2$ is 8-methoxy.

17. The method according to claim 14 wherein $R_2$ is 9-fluoro.

18. A pharmaceutical composition active as an antiallergy agent comprising a pharmaceutically-acceptable carrier and a compound of the formula

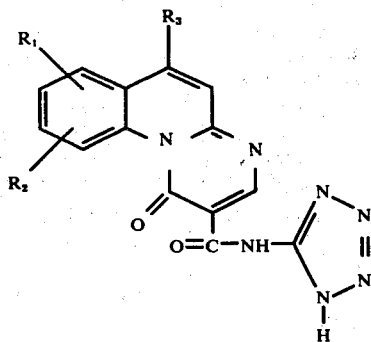

wherein each of $R_1$ and $R_2$ is selected from the group consisting of hydrogen, lower alkyl, lower alkoxy, chloro, and fluoro;

$R_1$ and $R_2$ when taken together are alkylenedioxy and are selected from the group consisting of methylenedioxy and ethylenedioxy;

$R_3$ is selected from the group consisting of chloro, bromo and lower alkoxy;

and the pharmaceutically-acceptable cationic salts thereof.

19. A composition according to claim 18 wherein each of $R_1$ and $R_2$ is hydrogen and $R_3$ is lower alkoxy.

20. A composition according to claim 18 wherein $R_1$ is hydrogen, $R_2$ is 9-lower alkoxy and $R_3$ is methoxy.

21. A composition according to claim 18 wherein $R_1$ is hydrogen, $R_2$ is fluoro and $R_3$ is methoxy.

22. A pharmaceutical composition as claimed in claim 18 in a form suitable for administration by inhalation.

23. A pharmaceutical composition as claimed in claim 18 comprising a solution or suspension of the antiallergy agent in water.

24. A pharmaceutical composition as claimed in claim 18 comprising a suspension of the antiallergy agent in a liquefied propellant.

25. A pharmaceutical composition as claimed in claim 18 comprising the solid antiallergy agent and a solid diluent.

* * * * *

UNITED STATES PATENT AND TRADEMARK OFFICE
CERTIFICATE OF CORRECTION

PATENT NO. : 4,017,625

DATED : April 12, 1977

INVENTOR(S) : Saul B. Kadin, New London, Conn.

It is certified that error appears in the above–identified patent and that said Letters Patent are hereby corrected as shown below:

Col. 15, line 2, "Suspension A" should read -- Suspension B -- ;

Col. 17, line 66, "hydrogen," should read -- selected -- .

Signed and Sealed this twenty-third Day of August 1977

[SEAL]

Attest:

RUTH C. MASON
Attesting Officer

C. MARSHALL DANN
Commissioner of Patents and Trademarks